United States Patent [19]
Lutey

[11] Patent Number: 6,132,777
[45] Date of Patent: Oct. 17, 2000

[54] BORATES USEFUL FOR THE PREVENTION/ MITIGATION OF MICROBIOLOGICALLY INFLUENCED CORROSION AND STAINING

[75] Inventor: Richard W. Lutey, Memphis, Tenn.

[73] Assignee: Buckman Laboratories International, Inc., Memphis, Tenn.

[21] Appl. No.: 08/841,852

[22] Filed: May 5, 1997

Related U.S. Application Data

[62] Division of application No. 08/231,715, Apr. 22, 1994, Pat. No. 5,654,012.
[51] Int. Cl.$^7$ .......................... A01N 59/14; A01N 59/16; C04B 14/36
[52] U.S. Cl. .......................... 424/641; 424/652; 424/617; 424/657; 424/658; 424/659; 424/660; 424/489; 106/717
[58] Field of Search ...................................... 424/652, 617, 424/641, 657, 658, 659, 660, 489; 106/18.3, 18.13, 717, 14.05, 14.39; 252/387

[56] References Cited

U.S. PATENT DOCUMENTS

| 4,180,508 | 12/1979 | Becker et al. .................... 260/326.5 C |
| 5,066,334 | 11/1991 | Pera et al. ............................... 106/462 |
| 5,227,360 | 7/1993 | Sherba et al. ........................... 504/152 |
| 5,314,719 | 5/1994 | Batdorf et al. ....................... 427/385.5 |
| 5,330,795 | 7/1994 | Batdorf et al. ....................... 427/393.6 |

FOREIGN PATENT DOCUMENTS

| 0 434 391 | 6/1991 | European Pat. Off. . |
| 1557789 | 2/1969 | France . |
| 2 103 752 | 4/1972 | France . |
| 63-289149 | 11/1988 | Japan . |

OTHER PUBLICATIONS

Webster's New World Dictionary of America English, 3rd colledge edition Neufeldt et al. (eds.), Simon & Schuster, Inc., New York, 1988, p. 134.

Biological Abstracts 83(3): 23038, Feb. 1, 1987; abstracting, Grant et al., "Evaluation of fungicidal paints, " Int. Biodeterior; 22(3), 1986, pp. 179–194.

Chemical Abstracts III: 44460, 1989; abstracting JP 63/289149, Nov. 25, 1988.

Bergey's Manual of Determinative Bacteriology, Ninth Edition, 1993, pp. 23–24.

"Busan® 11–M1 For Fire Resistance in Plastics, Paints, Textiles, Rubber, and Adhesives" Buckman Laboratories Product Information Brochure, Apr. 1992.

"Busan 11–M1 A Multifunctional Pigment for the Coatings Industry" Buckman Laboratories Product Information Brochure, Mar. 1993.

"Formulating Water–Based Coatings with Barium Metaborate Pigments" Buckman Laboratories Product Data Sheet, Nov. 1993.

Chemical Abstracts, vol. 83, No. 20, 1975, Abstract No. 165861h.

Chemical Abstracts, vol. 85, No. 4, 1976, Abstract No. 22803.

Chemical Abstracts, vol. 113, No. 14, 1990, Abstract No. 120011.

PCT International Search Report dated Aug. 8, 1995.

Van Nostrand's Scientific Encyclopedia, $7^{th}$ edition, Van Nostrand Reinhold, New York, 1989, pp. 732–733.

*Primary Examiner*—John Pak
*Attorney, Agent, or Firm*—Kilyk & Bowersox, P.L.L.C.

[57] ABSTRACT

The present invention discloses methods for 1) preventing and/or mitigating microbiologically influenced corrosion (MIC) and 2) controlling and/or reducing the growth of at least one anaerobic, facultative anaerobic, or microaerophilic microorganism, which includes the step of adding or applying a composition containing a borate salt to an area susceptible to MIC and/or growth of anaerobic, facultative anaerobic, or microaerophilic microorganisms, in an effective amount to 1) control and/or reduce the growth or 2) to prevent and/or mitigate the corrosion. The present invention also discloses various means of using the compositions of the present invention which contain borate salts and further sets forth methods for preventing and/or mitigating staining caused, at least in part, by at least one anaerobic, facultative anaerobic, or microaerophilic microorganism.

8 Claims, No Drawings

BORATES USEFUL FOR THE PREVENTION/ MITIGATION OF MICROBIOLOGICALLY INFLUENCED CORROSION AND STAINING

This is a divisional of application Ser. No. 08/231,715 filed Apr. 22, 1994 now U.S. Pat. No. 5,654,012

BACKGROUND OF THE INVENTION

The present invention relates to certain compositions and methods useful for preventing and/or mitigating microbiologically influenced corrosion and staining occurring, for example, in a sealed environment.

Microbiologically influenced corrosion (MIC) of the internal surfaces of equipment such as pipes, tanks, and heat transfer components, in addition to non-MIC electrochemically influenced corrosion, results in extensive "remove and replace" maintenance projects. This is usually very costly and time consuming.

An alternative procedure used in some situations is to install an insert or lining, in situ, composed of a resin (e.g., epoxy or vinyl esters) system that forms a barrier between the host component, e.g. transmission pipe line, and the fluid being transported through the pipe line. Once in place, this lining provides a means of mitigating the effect of the corrosion. However, it may not prevent the corrosion mechanism from continuing to degrade the host component.

Wide-spread forms of MIC occur where anaerobic conditions exist. MIC is often identified as including pitting corrosion or "under-deposit" corrosion.

Microorganisms involved include sulfate reducing bacteria (SRB) and Clostridium types which produce $H_2S$ or $H_2$ that attack the metal. The microorganisms' source of inoculum is virtually unlimited. However, the corrosion caused by their growth occurs only when specific conditions exist such as an oxygen free environment. The microorganisms can grow to very large populations in localized sites and attack the host component, e.g., metal, causing a very aggressive corrosion condition.

Furthermore, inserting a lining or barrier on the inner surface of a pipe line may provide the ideal anaerobic environment for microorganisms to grow and subsequently influence corrosion of the host component. Cleaning and removing the debris and corrosion by-products, found on inner surfaces where the lining would interface, is a necessary step to insure proper application. However, this cleaning typically will not eliminate the microorganism inoculum source. Even under the best case conditions where cleaning was exceptionally complete, and the installation of the lining was flawless, the potential for MIC to be initiated or to resume activity is very high.

A four year study made under actual plant operating conditions examined various corrosion mechanisms involved with typical service water system materials of construction. Corrosion coupons were included as part of the test samples. Some of the coupons were placed in a position where the insert liner was placed as a barrier to provide the host component protection from corrosion. A few of the liner samples were intentionally flawed to simulate installation problems. Unlike actual plant installation of the liner, however, the base materials were coated with an epoxy adhesive to insure the liner material was attached to the coupon. It was known that the epoxy adhesive was not a specific moisture barrier; however, it should have provided some additional protection against corrosion of the base material. Some observations made during the study that related to MIC included:

1. Coupons in stagnant, intermittent, and continuous flow positions were susceptible to MIC.

2. The lack of tuberculation formation does not imply MIC has not occurred.

3. If there is damage to the coating or lining and the felt is not impregnated with resin, water will wick through and promote corrosion of the base metal.

4. Due to the specific water chemistry of the test site, no significant corrosion under the liner occurred, but other sites with different chemistries could experience severe corrosion.

Another type of liner that creates an anaerobic environment is the liner used in swimming pools. These types of liners are affected by staining caused, in part, by facultative anaerobic, anaerobic, or microaerophilic microorganisms.

The staining can be described as intense black-brown or gray isolated spots, or more diffuse gray discoloration of the vinyl surface and blotchy in appearance. The discolorations are, for example, located below the water level usually on the sloping sides and on the bottom of the pools. Staining has been observed at depth of 2–3 feet and to 9 feet. In most cases, the staining was localized where the back-side surface of the liner came into direct contact with the cement/sand or cement/vermiculite base used to form the pool in-ground and upon which the vinyl liner was placed. Rarely was staining observed on water-side surfaces where the back-side surfaces were in direct contact with galvanized metal vertical walls, or poured concrete/concrete block vertical walls. Stereoscopic microscope examination of the water-side stained surfaces of the liner indicated that the stain was not specifically the result of substances adhering to or adsorbed onto the vinyl surface which was exposed to the pool water. In fact, these observations indicated that the stain appeared to originate on the back-side surface and diffuse through the vinyl, appearing as a disfigurement on the water-side surface.

Staining occurred in pools routinely treated with oxidizing biocides such as hypochlorite salts, tri/dichloroisocyanurate, and bromine compounds to control growth of algae and other microorganisms. It also occurred in pools treated with nonoxidizing algicides such as quaternary ammonium salts and polyquat compounds often used in conjunction with oxidizing biocides. These investigations indicated that the chemical characteristics of the pool water (such as pH, hardness, and alkalinity) had no correlation to the occurrence of the staining. Staining was observed most frequently on liners that had been in place for 5–15 years. The stains usually appeared gradually over that time. However, it was also reported that liners used to replace the stained liners became stained in the same general location within a period as short as one year after replacement.

In addition to promoting an anaerobic environment, the inherent physical characteristics of liners and the procedures used to install them provide many ideal opportunities for the growth of anaerobic, facultative anaerobic, or microaerophilic microorganisms which can lead to staining or MIC.

The need to prevent MIC or staining or to mitigate an existing MIC or staining situation is clear. The key to preventing or mitigating MIC or staining is to prevent the growth of the microorganisms responsible for the MIC or staining. This can be done by including into the susceptible environment a biocide-biostat with efficacy in controlling or reducing the growth of facultative anaerobic, anaerobic, or microaerophilic microorganisms. The chemical characteristics of the biocide-biostat should preferably have the following properties: long persistency, minimum water solubility, passive to composition materials of the lining system and the host component (e.g., metal), non-hazardous, and environmentally acceptable.

Accordingly, a goal of the present invention is to provide compositions capable of preventing and/or mitigating microbiologically influenced corrosion, over prolonged periods of time. An additional goal of the present invention is to provide a method for biostatically reducing the growth of anaerobic, facultative anaerobic, or microaerophilic microorganisms. Another goal of the present invention is to provide a method for preventing and/or mitigating microbiologically influenced corrosion. A further goal of the present invention is to provide a method for preventing and/or mitigating the type of staining described above.

Additional advantages of the present invention will be set forth in part in the description which follows, and in part will be apparent from the description, or may be learned by practice of the present invention. The goals and advantages of the present invention will be realized and attained by means of the elements and combinations particularly pointed out in the appended claims.

To achieve the above noted goals and in accordance with the purpose of the present invention, as embodied and broadly described herein, the present invention provides biocide-biostat compositions useful in 1) controlling and/or reducing the growth of an anaerobic, facultative anaerobic, or microaerophilic microorganisms and 2) preventing and/or mitigating microbiologically influenced corrosion or staining. The compositions contain a borate salt, preferably calcium metaborate, barium metaborate, calcium pyroborate, or mixtures thereof.

The present invention also provides a method for preventing and/or mitigating microbiologically influenced corrosion, for instance, in a sealed environment, which comprises the step of adding or applying a composition of the present invention to an area susceptible to MIC, e.g., inside a pipe to prevent and/or mitigate corrosion.

In addition, the present invention provides a method for controlling and/or reducing the growth of an anaerobic, facultative anaerobic, or microaerophilic microorganism which comprises the step of adding or applying a composition of the present invention to an area susceptible to the growth of the microorganism. Further, the present invention provides a method to prevent and/or mitigate staining caused by a microorganism comprising the step of adding or applying a composition of the present invention to an area susceptible to staining to prevent and/or mitigate such staining.

It is to be understood that both the foregoing general description and the following detailed description are exemplary only and are not restrictive of the present invention, as claimed.

DETAILED DESCRIPTION OF THE PREFERRED EMBODIMENT

With regard to the borate salts useful for the prevention/mitigation of microbiologically influenced corrosion or staining and also useful in controlling/reducing the growth of an anaerobic, facultative anaerobic, or microaerophilic microorganism, these borate salts should preferably have certain chemical characteristics including long persistency (e.g., remain in biologically active form for at least two years), a minimum water solubility (e.g., solubility in water in the range of about 0.1 to about 0.5 percent in water at 21° C.), be passive to composition materials of the lining system and the host component (e.g., metal), be non-hazardous, and environmentally acceptable. Metaborates, and preferably barium metaborate and calcium metaborate, meet these chemical characteristics and can be used, separately or as a mixture, for purposes of the present invention. One such commercially available barium metaborate is Busan 11-M1, available from Buckman Laboratories, Memphis, Tenn., which is a modified barium metaborate monohydrate. The typical properties of this metaborate which are preferred for purposes of the present invention are set forth in Buckman Technical Bulletins identified as "Busan 11 M1—A Multifunctional Pigment for the Coatings Industry" (Sep. 19, 1983), "Busan® 11 M1—Fire Resistance in Plastics, Paints, Textiles, Rubber, and Adhesives" (1992), and "Formulating Water-Based Coatings with Barium Metaborate Pigments" (1993), all incorporated in their entireties herein by reference. Other examples of borate salts include pyroborates and tetraborates such as calcium pyroborate. Besides the calcium and barium boron type salts described above, boron salts such as Na, Ammonium, Pb, Li, Mg, K, Sr, or Zn borates and boric acid can be used. U.S. Pat. No. 5,066,334, incorporated in its entirety herein by reference, sets forth several methods of making metaborates and pyroborates such as calcium metaborate. The borate salts set forth in the '334 patent can be used for purposes of the present invention. The solubility of the metaborates make them ideal for emulsions. These emulsions can be used in spray applications.

As these terms are used herein, "preventing and/or mitigating" microbiologically influenced corrosion, is to be understood that the present invention in effect "controls and/or reduces" the growth of at least one anaerobic, facultative anaerobic, or microaerophilic microorganism, responsible, at least in part, for the microbiologically influenced corrosion or staining. It is to be further understood that by "controlling" (i.e., preventing) the growth of at least one of these types of microorganisms, the growth of the microorganism is inhibited. In other words, there is no growth or essentially no growth of at least one anaerobic, facultative anaerobic, or microaerophilic microorganism. Thus, the substrates or materials susceptible to attack by these types of microorganisms are preserved from this attack and the resulting corrosion or staining caused by the microorganisms. Further, it is to be understood that by "reducing" the growth of at least one anaerobic, facultative anaerobic, or microaerophilic microorganism, the level of microorganisms present are biostatically reduced and/or maintained to a low level such that the microbiologically influenced corrosion or staining is mitigated, i.e., the corrosion or staining rate is slowed down or eliminated.

The microorganisms controlled and/or reduced by the present invention include anaerobic, facultative anaerobic, and microaerophilic fungi and bacteria. The terms anaerobic (i.e., anaerobe), facultative anaerobic (i.e., facultative anaerobe), and microaerophilic (i.e., microaerophile) as used herein are defined in Bergey's Manual of Determinative Bacteriology (Ninth Ed.) and these definitions are incorporated herein by reference. Examples of such microorganisms include, but are not limited to, sulfate reducing bacteria, Clostridium types which provide $H_2S$ or $H_2$ that attack a metal substrate, and Aureobasidium sp. that causes staining. Other examples include anaerobic, facultative anaerobic, and/or microaerophilic microorganisms included in the following genera: Pseudomonas, Arthrobacter Enterobacter, Xanthomonas, and Saccharomvces.

With regard to using borate salts of the present invention in preventing and/or mitigating MIC in an area susceptible to MIC, for instance in a sealed environment, e.g., pipe line system, the following preliminary procedure should preferably be followed.

In minimizing the impact of MIC in any type of system, whether it is to be lined or not, it is important to understand the mechanisms of MIC and what preliminary mitigation procedures should be considered. One of the first considerations for MIC mitigation in systems where a liner insert will be used, should be the pre-installation cleaning process. The host component, e.g., pipe, must be cleaned before installing the liner. Several cleaning techniques can be used and each has certain specific characteristics. The chemical composition of the materials to be removed by the cleaning is an important consideration, as is the material of construction of the component to be cleaned. Before selecting and implementing a cleaning procedure, it is suggested that laboratory test data on deposit analysis and corrosion data be conducted and reviewed. It would be prudent to refer to resource literature on recommended cleaning practices for industrial process water systems.

While it may not be necessary to return the host component to a "like new" condition before installing the liner, all debris, existing corrosion nodules, and macrofouling agents (such as mussels, barnacles, oysters, etc.) should be removed. This removal step not only removes as many of the MIC causing agents as possible, but also minimizes mechanical or physical damage such contaminants can cause to the liner.

However, even if cleaning is completed, endospore forming microorganisms can persist and still be present in an active or spore state. Under the best case conditions, assuming a properly cleaned pipe and a flawless liner installation, the potential for inter-annulus corrosion as a result of MIC still exists. Anaerobic, facultative anaerobic, and microaerophilic bacteria which include pit forming of sulfate reducing bacteria and Clostridium could find the conditions created by the installation of the liner appropriate for their survival and growth.

Even after installation, there can be voids between the liner and the host component. The exact cause of the void is dependent on many factors, one of which is the selection of resin chemistry. The epoxy resins are less vulnerable to shrinkage than the vinyl esters. Regardless of the resin used it is likely that there will not be a continuous bond between the liner and the host pipe. When a void exists, bulk water carrying bacterial inoculum could find its way into the inter-annulus area.

One point of inoculation would be where there is a flaw such as a tear in the felt or a hole in the elastomeric-coating on the internal diameter of the liner. This can cause wicking or seepage of raw water to the inter-annulus area. These flaws or entry points may exist to the extent that they allow continuous seepage of bulk water behind the liner and therefore provide repeated inoculation of MIC causing bacteria.

Less than 100% water tight seal is often found at flanges, lateral lines, and instrument penetrations. These leaks would also permit the continued exposure of the host component, e.g., pipe, to moisture and a continued inoculum. The potential for other corrosion mechanisms to become involved results from the leaks as well.

Thus, the benefits of the present invention include being able to use the lining to mitigate an existing corrosion condition without increasing the potential for MIC. This application will also prevent MIC, compensating for the inherent limitations of installing a flawless lining. The borate salts have been shown to provide a degree of non-MIC corrosion inhibition as well. In particular, the borate salts provide a sufficient source of alkalinity which neutralizes corrosion caused by acid or a low pH. In effect, the borate salts of the present invention act as pH buffers, which significantly lessen the rate of corrosion caused by acid or a low pH.

One way to apply the composition of the present invention is in the form of an emulsion of the borate salt which can be made in a liquid vehicle formulation that suspends the borate salt pigment in a flowable form. Suspending agents such as hydroxymethyl cellulose can be formulated with the borate salt. Preferred emulsions are set forth in the Example which follows. This fluid can then, for instance, be sprayed onto the surface areas susceptible to MIC, growth of anaerobic, facultative anaerobic, or microaerophilic microorganisms and/or staining, which are preferably cleaned. In other words, and referring to a specific use, the fluid is sprayed on the component to be treated (e.g., pipe, in-ground pool substrate base) to which the lining is applied. The spray application can be achieved in a number of ways and are known by those skilled in the art. Pipe line applications can also be done by the use of robotic sprayers following cleaning prior to the installation of the lining. Tanks and other similar components can then be spray painted following cleaning.

The compositions of the present invention can also be used to prevent the initial occurrence of staining on such surfaces as vinyl pool liner surfaces caused, at least in part, by the growth of anaerobic, facultative anaerobic, or microaerophilic microorganisms on the base substrate over which the liner is placed. While the specific liner discussed herein is a pool liner, other substrates susceptible to similar attack by anaerobic, facultative anaerobic, or microaerophilic microorganisms are encompassed by the present invention. The compositions of the present invention can be dry-blended into the sand/cement or vermiculite/cement substrate used as the base of in-ground pools. Under preferred circumstances, this should be done when the pool liner is initially installed. The compositions of the present invention should preferably be added to the base substrate at a level of about one pound of borate salt (as commercially received) per about 45 pounds of cement mixed with about 145 pounds of sand (or about 20 pounds of vermiculite).

The compositions of the present invention can also be used to prevent the initial occurrence or reoccurrence of staining on liner surfaces (e.g., vinyl pool liners) caused, at least in part, by the growth of anaerobic, facultative anaerobic, or microaerophilic microorganisms on the base substrate over which the liner is placed. The borate salt of the present invention should be applied to the surface of the base substrate during construction of the pool or during the installation of a replacement liner. Application can be made by spraying or brush applying a water-based latex formulation containing approximately 18% solids by we ght of the borate salt. This formulation should preferably be applied at a coverage rate of one gallon per 100 square feet of base substrate surface, providing approximately 1.8 pounds of borate salt per 100 square foot of substrate surface. Generally, about 1.5 pounds to about 3.6 pounds of borate salt per 100 square feet of substrate surface can be used.

The present invention will be further clarified by the following examples, which are intended to be purely exemplary of the present invention.

EXAMPLE

From an in-ground swimming pool in Memphis, Tenn. samples of stained vinyl were obtained and examined using microscopic and microbiological isolating culturing techniques known to those skilled in the art. Samples of the sand/cement base substrate where the stained vinyl was in contact were also examined using similar techniques. Several different types of microorganisms were observed growing on the back-side of the vinyl liner. Many of the same microorganisms were found in the substrate, and appeared to be growing in the first few inches in depth from the interface of the substrate and the vinyl. Samples of the sand-cement substrate, collected from areas where no staining existed, were also examined. Scattered hyphae, but no dense mycelia, were observed. Back-side surfaces of the vinyl, where no staining existed, were also examined. Although these surfaces were not sterile, no hyphae or fungal mycelial masses were observed.

The dominate microflora associated with staining were "Fungi Imperfecti" (molds). No sporulation was observed "in-vivo." However, when isolates of mycelia, collected from the samples, were cultured on mycophil agar, sporulation occurred. Sporulation also occurred from mycelia on samples of vinyl when incubated at 37° C. in mold free humidity chambers.

Based on the "in-vitro" sporulation, the dominant microaerophilic, facultative anaerobic and anaerobic fungi were characterized as genera in the Moniliacese, e.g. Aureobasidium sp., Torula sp., Phialomyces sp. Aureobasidium sp. and Phialomyces sp. seemed to overgrow the microflora in-vitro. Some bacteria were present in the microflora isolated from the samples but did not appear to be a significant factor in the occurrence of the problem.

Efforts to extract and characterize chemically the substance contributing to the discoloration were not successful. Both organic and aqueous solvents were used to try to remove the discoloration from the vinyl without success. Strong oxidizing solutions, i.e., 5 percent NaOCl, bleached the stain out, but it also bleached out the coloring of the vinyl. Infrared analysis comparisons of extracts from both stained vinyl and non-stained vinyl showed no differences.

Attempts were made to reproduce the staining on pool liner vinyl specimens under laboratory conditions. A sand/cement substrate was prepared and inoculated with isolates of Aureobasidium sp. Samples of vinyl were placed in direct contact with the inoculated substrate and incubated at 32° C.± in a humid environmental chamber for 90 days. Extensive growth of fungus occurred both on the substrate and over the surface of the vinyl in contact with the substrate.

However, no disfiguration of the vinyl occurred under the conditions of the test.

From the results and observations made, it was theorized that the staining was in some way related to the growth of typically occurring soil-born fungi such as Aureobasidium sp. and Phialomyces sp. on the substrate under microaerophilic conditions in contact with the back-side surfaces of the vinyl. It was further theorized that as a result of the growth of the fungi, a substance, not fungal tissue, was produced "in-vivo" by the mycelial mat that diffused into the vinyl and appeared as a stain or disfigurement on the water-side surface of the vinyl liner.

"In-Vivo" Studies

An in-ground vinyl liner pool, located in Memphis, Tenn. where a staining problem had previously occurred, was selected for in-vivo studies. This stained pool liner was originally installed on a sand/cement base 13 years prior to liner replacement. Staining appeared on the "floor" of the shallow end (3 foot depth) and on the sloping sides of the deep end (5–7 foot depth) during a period of three years prior to replacement. Although staining may have occurred earlier, it was not readily observed. During the three years prior to liner replacement, chemicals (e.g. phosphonates and acrylate compounds) were added to the pool water to remove or prevent the staining. That treatment was not successful.

When the original liner was removed, observations and examinations described above were made. Prior to installing the replacement liner, two areas three feet by three feet in the shallow end where staining of the original liner had occurred were selected as test sites. The original sand/cement substrate on one site was moved to a depth of three inches. This was replaced with a substrate composed of:

140 pounds—washed masonry sand;
45 pounds—type A portland cement; and
1 pound=BUSAN 11-M1® modified barium metaborate monohydrate.

The mixture was dry blended, moistened slightly, and troweled into the floor of the pool. No treatment other than troweling the surface was done to the second test site. Following this, the replacement liner was installed in a routine manner.

Visual observations of the two test sites have been made periodically during four swimming seasons subsequent to the liner replacement (i.e. a 36 month period). No obvious staining has occurred at either of the two test sites. However, there appeared to be very slight indications that staining may be reappearing at the "deep end" location where staining had also occurred on the original liner.

"In Vitro" Studies

Laboratory studies were done to determine the efficacy of BUSAN 11-M1® modified barium metaborate monohydrate in preventing the growth of fungi on a sand/cement or sand/vermiculite substrate. The following tests were done:

New Pool Liner Procedures: Dry Blend

Based on the above results, it was assumed that inclusion of BUSAN 11-M1® modified barium metaborate monohydrate into the base substrate mixture will inhibit the growth of fungi that cause staining. This assumption was tested by dry blending BUSAN 11-M1® modified barium metaborate monohydrate into a sand/cement mixture at a ratio (by weight) of one part BUSAN 11-M1® modified barium metaborate monohydrate, 45 parts Type A portland cement, 140 parts washed masonry sand. This mixture was inoculated with a spore/mycelial suspension of Aureobasidium sp., covered with a specimen of vinyl pool liner, and incubated in a humid environmental chamber at 32° C.±for 90 days. During the incubation period, the test substrate was moistened to maintain a wet interface between the liner and the substrate.

The same substrate without BUSAN 11-M1® modified barium metaborate monohydrate was prepared, inoculated, incubated, and moistened in an identical manner as that with BUSAN 11-M1® modified barium metaborate monohydrate.

Visual observations were made after 30, 60, and 90 days incubation. The surfaces of the substrates were examined using stereoscopic microscope techniques. Substantial hyphal development and conidia germination were observed after 30 days on surfaces of the substrate that contained no BUSAN 11-M1® modified barium metaborate monohydrate. No hyphal development was observed on the substrate containing BUSAN 11-M1® modified barium metaborate monohydrate. Some hyphae were observed on the outer surfaces of the vinyl opposite to the surface in contact with the substrate containing BUSAN 11-M1® modified barium metaborate monohydrate. Hyphae were observed on both the contact surface and outer surface of the vinyl in contact with the substrate containing no BUSAN 11-M1® modified barium metaborate monohydrate.

Similar results were observed at examinations made after 60 and 90 days incubation. Sporulation of the Aureobasidium sp. and a few airborne contaminating fungi was observed after 60 days incubation on the specimens that did not contain BUSAN 11-M1® modified barium metaborate monohydrate.

After 90 days of incubation sporulation was observed on the following:

Substrate surface containing no BUSAN 11-M1® modified barium metaborate monohydrate;

Vinyl surface in contact with substrates containing no BUSAN 11-M1® modified barium metaborate monohydrate;

Outer surface of vinyl in contact with substrate containing no BUSAN 11-M1® modified barium metaborate monohydrate;

Outer surface of vinyl in contact with substrate containing BUSAN 11-M1® modified barium metaborate monohydrate.

After 90 days of incubation no sporulation was observed on the following:

Substrate surface containing BUSAN 11-M1® modified barium metaborate monohydrate; and Vinyl surface in contact with substrate containing BUSAN 11-M1® modified barium metaborate monohydrate.

From these observations, the following conclusions were made:

BUSAN 11-M1® modified barium metaborate monohydrate inhibits the development of hyphae and prevents sporulation of Aureobasidium sp. on the surface of the substrate when dry blended into the substrate;

BUSAN 11-M1® modified barium metaborate monohydrate inhibits sporulation of Aureobasidium sp. on vinyl surfaces directly in contact with x substrates containing BUSAN 11-M1® modified barium metaborate monohydrate; and BUSAN 11-M1® modified barium metaborate monohydrate does not mitigate or diffuse into vinyl liner when in direct contact with substrate containing BUSAN 11-M1® modified barium metaborate monohydrate. This was concluded from evidence of growth by the fungus on the opposite surface of vinyl in contact with substrate containing BUSAN 11-M1® modified barium metaborate monohydrate.

Replacement Pool Liner Procedures—Latex Spray

An alternative way to dry blending BUSAN 11-M1® modified barium metaborate monohydrate into the base substrate was investigated. The need for this alternative was based on eliminating the requirement for replacing existing base substrate in pools when liner replacements were being made. Based on the above successful results, it was assumed that a topical application of BUSAN 11-M1® modified barium metaborate monohydrate to the surface of a base substrate already in place would inhibit the growth of stain causing fungi. This hypothesis was tested by the following procedure.

A latex emulsion formulation containing BUSAN 11-M1® modified barium metaborate monohydrate was developed that could be sprayed or brush applied to the base substrate surfaces. The formulation was as follows:

| Material | Percent of Total Weight |
|---|---|
| Cellosize Hydroxyethyl Cellulose (1% sol. QP-15,000 M Union Carbide HEC) | 76.8 |
| BUSAN 11-M1 ® modified barium metaborate monohydrate - as received | 18.3 |
| Acrylic Latex - UV-433 (Union Carbide UCAR Vehicle 443 total solids - 41% by weight) | 4.8 |
| Busperse 39 - as received (Buckman Labs - Sodium Polyacrylate) | 0.1 |

This formulation is aqueous based, with a viscosity suitable for spray-application using conventional spray paint application equipment or brush application.

Formulation/manufacturing equipment, as well as spray application equipment, can readily be cleaned by simply flushing and rinsing with water. Product stability was confirmed by traditional procedures used to test stability of commercial latex emulsion paint and coating products. The formulation should be mixed in the container received prior to application.

A laboratory scale test of the efficacy of BUSAN 11-M1® modified barium metaborate monohydrate in this formulation was made in conjunction with the tests made in the dry-blend procedures, described above. The formulation containing BUSAN 11-M1® modified barium metaborate monohydrate was spray applied to the test sand/cement substrate at a level equivalent to one gallon formulation per 100 square feet of substrate surface. This provided a level of BUSAN 11-M1® modified barium metaborate monohydrate of 1.8 pounds per 100 square feet of substrate surface. The formulation applied to the substrate was allowed to partially dry (i.e. stand for four hours) prior to inoculation and incubation. The same observations made with the dry-blend procedure were done after 30, 60, and 90 days. Results and observations were compared to a control preparation of the formulation containing no BUSAN 11-M1® modified barium metaborate monohydrate.

The observations confirmed that BUSAN 11-M1® modified barium metaborate monohydrate applied in a water-based latex emulsion, at a level of approximately 1.8 pounds of BUSAN 11-M1® modified barium metaborate monohydrate per 100 square feet of substrate surface, will inhibit the growth of Aureobasidium sp. under the conditions tested.

Other latex emulsion formulations containing BUSAN 11-M1® modified barium metaborate monohydrate include:

| Material | Percent of Total Weight |
|---|---|
| Formulation 2 | |
| 1% QR 708 sol. in water (urethane thickener-Union Carbide) | 76.8 |
| BUSAN 11-M1 ® modified barium metaborate monohydrate | 18.3 |
| Acrylic latex MV-23 (43% solids) (Rohm and Haas) | 4.6 |
| Busperse 39 (Buckman Laboratories) | 0.1 |
| Ethylene glycol monobutyl ether (film former) | 0.2 |

-continued

| Material | Percent of Total Weight |
|---|---|
| Formulation 3 | |
| 2% RM 1020 sol in water | 77.0 |
| (Rohm & Haas) | |
| BUSAN 11-M1 ® modified barium metaborate monohydrate | 18.3 |
| Aquamac 430 (44.5% solids) | 4.4 |
| (McWhorter Acrylic emulsion) | |
| Tamol 850 | 0.1 |
| (Rohm & Haas) | |
| Ethylene glycol monobutyl ether | 0.2 |
| Formulation 4 | |
| 1.2% QP - 30000 HEC in water | 77.0 |
| (Union Carbide) | |
| BUSAN 11-M1 ® modified barium metaborate monohydrate | 18.3 |
| Neocryl A-625 | 4.4 |
| (45% sol. Zeneca Resins) | |
| BSI 75 | 0.1 |
| (Buckman Laboratories) | |
| Ethylene glycol monobutyl ether | 0.2 |
| Formulation 5 | |
| Natrosol 250 HR HEC | 76.0 |
| (1% in sol.) (Aqualon, Inc.) | |
| BUSAN 11-M1 ® modified barium metaborate monohydrate | 18.3 |
| Acrylic Resin Neocryl A-640 | 4.0 |
| (40% solids, Zeneca Resins) | |
| Orotan 930 | 0.1 |
| (Rohm & Haas) | |
| Ethylene glycol monobutyl ether | 0.2 |
| Formulation 6 | |
| 2% MPA 1075 in water | 77.5 |
| (Bentonite, Rheox) | |
| BUSAN 11-M1 ® modified barium metaborate monohydrate | 18.3 |
| Synthemul 40-412 | 3.9 |
| (50% solids, Reichhold | |
| Colloid 226/35 Dispersant | 0.1 |
| (Allied Colloids) | |
| Ethylene glycol monobutyl ether | 0.2 |

SUPPLEMENTAL STUDIES

Vinyl Liner Compatibility

To confirm the compatibility of continuous contact of vinyl liner surfaces with substrates containing BUSAN 11-M1® modified barium metaborate monohydrate, a series of observations have been made. The physical appearance of the liner samples used in the efficacy studies were examined and compared to new liner samples. These samples were also compared to those in contact with substrate containing no BUSAN 11-M1® modified barium metaborate monohydrate. New vinyl liner samples were also placed in direct contact with moistened BUSAN 11-M1® modified barium metaborate monohydrate (as received) after a period of 150 days, no differences in the physical appearance of any of these vinyl samples could be distinguished. There is no past history information that would indicate any incompatibility problems and BUSAN 11-M1® modified barium metaborate monohydrate is used commercially as an additive in substrates fabricated with various vinyl resins.

BARIUM LEACHING STUDIES

The question of BUSAN 11-M1® modified barium metaborate monohydrate, as used in the proposed applications, contributing to hazardous levels of soluble Ba in ground waters was also addressed. Samples of the substrates used in the efficacy studies were analyzed by an independent laboratory for soluble Ba in leachate. The tests were performed in accordance with the Federal Register Vol. 45, No. 98, Part 261 "Identification and Listing of Hazardous Waste," Subpart C, 261.24. The results indicated that barium levels in the leachates are less than 5.0 mg/L.

This level is well below the level of "greater than 100 mg/L" which is the lower limit that the EPA classifies as hazardous.

Other embodiments of the present invention will be apparent to those skilled in the art from consideration of the specification and practice of the present invention disclosed herein. It is intended that the specification and examples be considered as exemplary only, with a true scope and spirit of the present invention being indicated by the following claims.

What is claimed:

1. A dry blend mixture useful in controlling or mitigating staining of a liner in contact with the mixture caused in part by at least an anaerobic, facultative anaerobic, or microaerophilic microorganism, said dry blend mixture comprising: a) sand and/or vermiculite, b) dry cement, and c) an amount of borate salt effective in controlling or mitigating staining caused by the microorganism.

2. The mixture of claim 1, wherein the borate salt is a sodium borate, ammonium borate, lead borate, lithium borate, magnesium borate, potassium borate, strontium borate, zinc borate, or boric acid, or mixtures thereof.

3. The mixture of claim 1, wherein the borate salt is a metaborate salt, a pyroborate salt, a tetraborate salt, or mixture thereof.

4. The mixture of claim 3, wherein the borate salt is a metaborate salt.

5. The mixture of claim 4, wherein the metaborate salt is calcium metaborate or barium metaborate.

6. The mixture of claim 1 wherein said mixture is present at a ratio of about one pound of said borate salt, per about 45 pounds of said cement, and about 145 pounds of said sand or about 20 pounds of said vermiculite per pound of borate salt.

7. The mixture of claim 1 wherein said mixture consist essentially of one pound of said borate salt, per about 45 pounds of said cement, and about 145 pounds of said sand or about 20 pounds of said vermiculite per pound of borate salt.

8. A method of applying a pool liner in an in-ground pool, comprising applying the dry blend mixture of claim 1 to the floor of an in-ground pool, and applying a pool liner to the dry blend mixture.

* * * * *